US011363990B2

(12) United States Patent
Tao et al.

(10) Patent No.: US 11,363,990 B2
(45) Date of Patent: Jun. 21, 2022

(54) SYSTEM AND METHOD FOR NON-CONTACT MONITORING OF PHYSIOLOGICAL PARAMETERS

(71) Applicant: ARIZONA BOARD OF REGENTS ON BEHALF OF ARIZONA STATE UNIVERSITY, Scottsdale, AZ (US)

(72) Inventors: Nongjian Tao, Fountain Hills, AZ (US); Dangdang Shao, Tempe, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 1102 days.

(21) Appl. No.: 15/826,224

(22) Filed: Nov. 29, 2017

(65) Prior Publication Data

US 2018/0140255 A1 May 24, 2018

Related U.S. Application Data

(63) Continuation of application No. 14/213,236, filed on Mar. 14, 2014, now abandoned.

(Continued)

(51) Int. Cl.
*A61B 5/00* (2006.01)
*A61B 5/024* (2006.01)
(Continued)

(52) U.S. Cl.
CPC ............ *A61B 5/7239* (2013.01); *A61B 5/004* (2013.01); *A61B 5/0077* (2013.01); *A61B 5/024* (2013.01);
(Continued)

(58) Field of Classification Search
CPC ..... A61B 5/7239; A61B 5/004; A61B 5/0077; A61B 5/024; A61B 5/0816; A61B 5/087; A61B 5/1128; A61B 5/113
See application file for complete search history.

(56) References Cited

U.S. PATENT DOCUMENTS 5,974,340 A * 10/1999 Kadhiresan ........ A61N 1/36542
607/18
7,035,432 B2 * 4/2006 Szuba .................. A61B 5/7275
600/595

(Continued)

FOREIGN PATENT DOCUMENTS

WO    2008148025 A1    12/2008
WO    2009132262 A1    4/2009

(Continued)

OTHER PUBLICATIONS

Jonathan et al., (2011), Cellular phone-based photoplethysmographic imaging, J. Biophotonics 4(5): 293-296.

(Continued)

*Primary Examiner* — Catherine B Kuhlman
*Assistant Examiner* — Sean A Frith
(74) *Attorney, Agent, or Firm* — Polsinelli PC

(57) ABSTRACT

A system and method for monitoring one or more physiological parameters of a subject under free-living conditions is provided. The system includes a camera configured to capture and record a video sequence including at least one image frame of at least one region of interest (ROI) of the subject's body. A computer in signal communication with the camera to receive signals transmitted by the camera representative of the video sequence includes a processor configured to process the signals associated with the video sequence recorded by the camera and a display configured to display data associated with the signals.

25 Claims, 6 Drawing Sheets

Related U.S. Application Data

(60) Provisional application No. 61/784,646, filed on Mar. 14, 2013.

(51) Int. Cl.
*A61B 5/08* (2006.01)
*A61B 5/087* (2006.01)
*A61B 5/11* (2006.01)
*A61B 5/113* (2006.01)

(52) U.S. Cl.
CPC ............ *A61B 5/087* (2013.01); *A61B 5/0816* (2013.01); *A61B 5/113* (2013.01); *A61B 5/1128* (2013.01)

(56) References Cited

U.S. PATENT DOCUMENTS

| | | | |
|---|---|---|---|
| 7,785,001 | B2 | 8/2010 | Tao et al. |
| 8,416,417 | B2 | 4/2013 | Foley et al. |
| 8,545,683 | B2 | 10/2013 | Tao et al. |
| 8,668,874 | B2 | 3/2014 | Tao et al. |
| 9,581,561 | B2 | 2/2017 | Tao et al. |
| 9,909,993 | B2 | 3/2018 | Tao et al. |
| 10,078,074 | B2 | 9/2018 | Tsow et al. |
| 10,078,795 | B2 | 9/2018 | Tao et al. |
| 10,143,401 | B2 | 12/2018 | Tao et al. |
| 10,209,232 | B2 | 2/2019 | Forzani et al. |
| 10,222,372 | B2 | 3/2019 | Tao et al. |
| 10,401,298 | B2 | 9/2019 | Tao et al. |
| 10,408,757 | B2 | 9/2019 | Tao et al. |
| 10,413,226 | B2 | 9/2019 | Tao et al. |
| 2004/0071337 | A1* | 4/2004 | Jeung .................. A61N 5/1049 600/534 |
| 2005/0234331 | A1 | 10/2005 | Sendai |
| 2006/0279428 | A1* | 12/2006 | Sato ..................... A61B 5/0064 340/575 |
| 2009/0292220 | A1* | 11/2009 | Miyake ................ A61B 6/5217 600/534 |
| 2010/0061596 | A1* | 3/2010 | Mostafavi .............. A61B 5/113 382/107 |
| 2010/0063419 | A1* | 3/2010 | Mostafavi .............. A61B 90/36 600/587 |
| 2011/0144517 | A1* | 6/2011 | Cervantes ................ A61B 5/08 600/538 |
| 2011/0158386 | A1* | 6/2011 | Payne ...................... G06T 7/11 378/54 |
| 2011/0251493 | A1* | 10/2011 | Poh ...................... G06K 9/624 600/477 |
| 2012/0113278 | A1* | 5/2012 | Okada ................. H04N 13/239 348/208.4 |
| 2013/0002832 | A1* | 1/2013 | Lasenby ................ G01B 11/16 348/51 |
| 2013/0156267 | A1* | 6/2013 | Muraoka ............... G06T 7/0016 382/103 |
| 2013/0211261 | A1* | 8/2013 | Wang .................... A61B 6/5217 600/476 |
| 2013/0218028 | A1* | 8/2013 | Mestha ............... A61B 5/02125 600/479 |
| 2015/0029321 | A1* | 1/2015 | Imamura ............... G06K 9/4661 348/77 |
| 2015/0216466 | A1 | 8/2015 | Kronberg et al. |
| 2015/0320338 | A1* | 11/2015 | Kane ..................... A61B 5/0826 600/533 |
| 2015/0379370 | A1* | 12/2015 | Clifton ................. A61B 5/0075 382/128 |
| 2019/0082972 | A1 | 3/2019 | Tao et al. |
| 2019/0094146 | A1 | 3/2019 | Tao et al. |
| 2019/0170748 | A1 | 6/2019 | Tao et al. |
| 2019/0239761 | A1 | 8/2019 | Tao et al. |
| 2019/0257802 | A1 | 8/2019 | Forzani et al. |
| 2019/0325257 | A1 | 10/2019 | Tao et al. |
| 2020/0000370 | A1 | 1/2020 | Tao et al. |
| 2020/0022628 | A1 | 1/2020 | Tao et al. |

FOREIGN PATENT DOCUMENTS

| | | |
|---|---|---|
| WO | 2009064985 A1 | 5/2009 |
| WO | 2010030874 A1 | 3/2010 |
| WO | 2010036940 A2 | 4/2010 |
| WO | 2010141610 A1 | 12/2010 |
| WO | 2013019843 A3 | 2/2013 |
| WO | 2014116604 A1 | 7/2014 |
| WO | 2015102902 A2 | 7/2015 |
| WO | 2015103459 A1 | 7/2015 |
| WO | 2017156084 A2 | 9/2017 |
| WO | 2018057753 A1 | 3/2018 |
| WO | 208170009 A1 | 9/2018 |
| WO | 2019136097 A1 | 7/2019 |

OTHER PUBLICATIONS

Allen, J. et al., "Age-related changes in peripheral pulse timing characteristics at the ears, fingers and toes", Journal of Human Hypertension, Nov. 2002 (available online Oct. 2002), vol. 16, No. 10, pp. 711-717 <DOI:10.1038/sj.jhh.1001478>.

Babchenko, A. et al., "Increase in pulse transit time to the foot after epidural anaesthesia treatment", Medical and Biological Engineering and Computing, Nov. 2000, vol. 38, pp. 674-679 <DOI:10.1007/BF02344874>.

Baheti, P. et al., "An Ultra Low Power Pulse Oximeter Sensor Based on Compressed Sensing", Sixith International Workshop on Wearable and Implantable Body Sensor Networks (Berkeley, CA, Jun. 3-5, 2009), 2009 (Date added to IEEE Xplore Aug. 2009), pp. 144-148 <DOI:10.1109/BSN.2009.32>.

Boutouyrie, P. et al., "Assessment of pulse wave velocity", Artery Research, Feb. 2009 (available online Dec. 2008), vol. 3, No. 1, pp. 3-8 <DOI:10.1016/j.artres.2008.11.002>.

Bramwell, J. et al., "Velocity of transmission of the pulse-wave: and elasticity of arteries", The Lancet, May 1922 (available online Sep. 2003), vol. 199, No. 5149, pp. 891-892 <DOI:10.1016/S0140-6736(00)95580-6>.

Brands, P. et al., "A noninvasive method to estimate pulse wave velocity in arteries locally by means of ultrasound", Ultrasound in Medicine & Biology, Dec. 1998 (available online Jan. 1999), vol. 24, No. 9, pp. 1325-1335 <DOI:10.1016/S0301-5629(98)00126-4>.

Chandrasekaran, V., "Measuring Vital Signs Using Smart Phones", University of North Texas, Master's Thesis, Dec. 2010 [retrieved Feb. 19, 2020], 146 pages, retrieved from the internet: <https://search.proquest.com/docview/863480203?pq-origsite=gscholar>.

De V Weir, J. et al., "New methods for calculating metabolic rate with special reference to protein metabolism", The Journal of Physiology, Aug. 1949, vol. 109, No. 1-2, pp. 1-9 <DOI:10.1113/jphysiol.1949.sp004363>.

Di Maria, C. et al., "Feasibility of monitoring vascular ageing by multi-site photoplethysmography", Computing in Cardiology (Krakow, Poland, Sep. 9-12, 2012), 2012 (Date added to IEEE Xplore Jan. 2013), pp. 817-820.

Garbey, M. et al., "Contact-Free Measurement of Cardiac Pulse Based on the Analysis of Thermal Imagery", IEEE Transactions on Biomedical Engineering, Aug. 2007 (Date of Publication Jul. 2007), vol. 54, No. 8, pp. 1418-1426 <DOI:10.1109/TBME.2007.891930>.

Hu, S. et al., "Feasibility of Imaging Photoplethysmography", International Conference on BioMedical Engineering and Informatics (Sanya, China, May 27-30, 2008), 2008 (Date added to IEEE Xplore Jun. 2008), pp. 72-75 <DOI:10.1109/BMEI.2008.365>.

Jago, J. et al., "Repeatability of peripheral pulse measurements on ears, fingers and toes using photoelectric plethysmography", Clinical Physics and Physiological Measurement, Nov. 1988, vol. 9, No. 4, pp. 319-329 <DOI:10.1088/0143-0815/9/4/003>.

Jin, S-H. et al., "A Robust Image Tracker based on Phase Correlation and Fourier-Mallin Transform", International Conference on Control, Automation and Systems (Seoul, South Korea, Oct. 14-17, 2008), 2008 (Date added to IEEE Xplore Dec. 2008), pp. 1028-1031 <DOI:10.1109/ICCAS.2008.4694650>.

Kwon, S. et al., "Validation of heart rate extraction using video imaging on a built-in camera system of a smartphone", Annual International Conference of IEEE Engineering in Medicine and

(56) References Cited

OTHER PUBLICATIONS

Biological Society (San Diego, CA, Aug. 28-Sep. 1, 2012), 2012 (Date added to IEEE Xplore Nov. 2012), pp. 2174-2177 <DOI:10.1109/EMBC.2012.6346392>.

Nitzan, M. et al., "The difference in pulse transit time to the toe and finger measured by photoplethysmography", Physiological Measurement, 2002 (published Dec. 2001), vol. 23, No. 1, pp. 85-93 <DOI:10.1088/0967-3334/23/1/308>.

Paradiso, R., "Wearable health care system for vital signs monitoring", IEEE EMBS Special Topic Conference on Information Technology Applications in Biomedicine (Birmingham, UK, Apr. 24-26, 2003), 2003 (Date added to IEEE Xplore Aug. 2003), pp. 283-286 <DOI:10.1109/ITAB.2003.1222533>.

Pickett, J. et al., "Pulse oximetry and ppg measurements in plastic surgery", Proceedings of the IEEE Engineering in Medicine and Biology Society (Chicago, IL, Oct. 30-Nov. 2, 1997), 1997 (Date added to IEEE Xplore Aug. 2002), pp. 2330-2332 <DOI:10.1109/IEMBS.1997.758831>.

Poh, M-Z. et al., "Advancements in Noncontact, Multiparameter Physiological Measurements Using a Webcam", IEEE Transactions on Biomedical Engineering, Jan. 2011 (Date of Publication Oct. 2010), vol. 58, No. 1, pp. 7-11 <DOI:10.1109/TBME.2010.2086456>.

Poh, M-Z. et al., "Non-contact, automated cardiac pulse measurements using video imaging and blind source separation", Optics Express, May 2010, vol. 18, No. 10, pp. 10762-10774 <DOI:10.1364/OE.18.010762>.

Poon, C. et al., "Wearable intelligent systems for E-Health", Journal of Computing Science and Engineering, Sep. 2011, vol. 5, No. 3, pp. 246-256 <DOI:10.5626/JCSE.2011.5.3.246>.

Rabben, S. et al., "An ultrasound-based method for determining pulse wave velocity in superficial arteries", Journal of Biomechanics, Oct. 2004 (available online Feb. 2004), vol. 37, No. 10, pp. 1615-1622 <DOI:10.1016/j.jbiomech.2003.12.031>.

Reisner, A. et al., "Utility of the Photoplethysmogram in Circulatory Monitoring", Anesthesiology, May 2008, vol. 108, No. 5, pp. 950-958 <DOI:10.1097/ALN.0b013e31816c89e1>.

Scully, C. et al., "Physiological Parameter Monitoring from Optical Recordings With a Mobile Phone", IEEE Transactions on Biomedical Engineering, Feb. 2012 (Date of Publication Jul. 2011), vol. 59, No. 2, pp. 303-306 <DOI:10.1109/TBME.2011.2163157>.

Shao, D. et al., "Noncontact Monitoring Breathing Pattern, Exhalation Flow Rate and Pulse Transit Time", IEEE Transactions on Biomedical Engineering, Nov. 2014 (Date of Publication Jun. 2014), vol. 61, No. 11, pp. 2760-2767 <DOI:10.1109/TBME.2014.2327024>.

Sun, Y. et al., "Noncontact imaging photoplethysmography to effectively access pulse rate variability", Journal of Biomedical Optics, Jun. 2013 (available online Oct. 2012), vol. 18, No. 6, article 061205, 9 pages <DOI:10.1117/1.JBO.18.6.061205>.

Takano, C. et al., "Heart rate measurement based on a time-lapse image", Medical Engineering & Physics, Oct. 2007 (available online Oct. 2006), vol. 29, No. 8, pp. 853-857 <DOI:10.1016/j.medengphy.2006.09.006>.

Verkruysse, W. et al., "Remote plethysmographic imaging using ambient light", Optics Express, Dec. 2008, vol. 16, No. 26, pp. 21434-21445 <DOI:10.1364/OE.16.021434>.

Won, B. et al., "A Touchscreen as a Biomolecule Detection Platform", Angewandte Chemie, Jan. 2012 (First published Oct. 2011), vol. 51, No. 3, pp. 748-751 <DOI:10.1002/anie.201105986>.

Yu, S-N. et al., "A Wireless Physiological Signal Monitoring System with Integrated Bluetooth and WiFi Technologies", IEEE Engineering in Medicine and Biology (Shanghai, China, Sep. 1-4, 2005), 2005 (Date added to IEEE Xplore Apr. 2006), pp. 2203-2206 <DOI:10.1109/IEMBS.2005.1616900>.

Zhao, F. et al., "Remote Measurements of Heart and Respiration Rates for Telemedicine", PLoS One, Oct. 2013, vol. 8, No. 10, article e71384, 14 pages <DOI:10.1371/journal.pone.0071384>.

\* cited by examiner

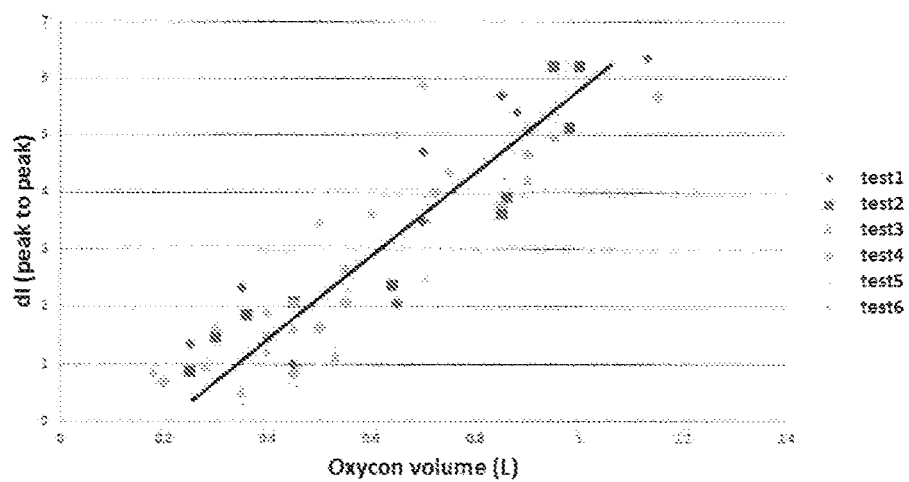
FIG. 7
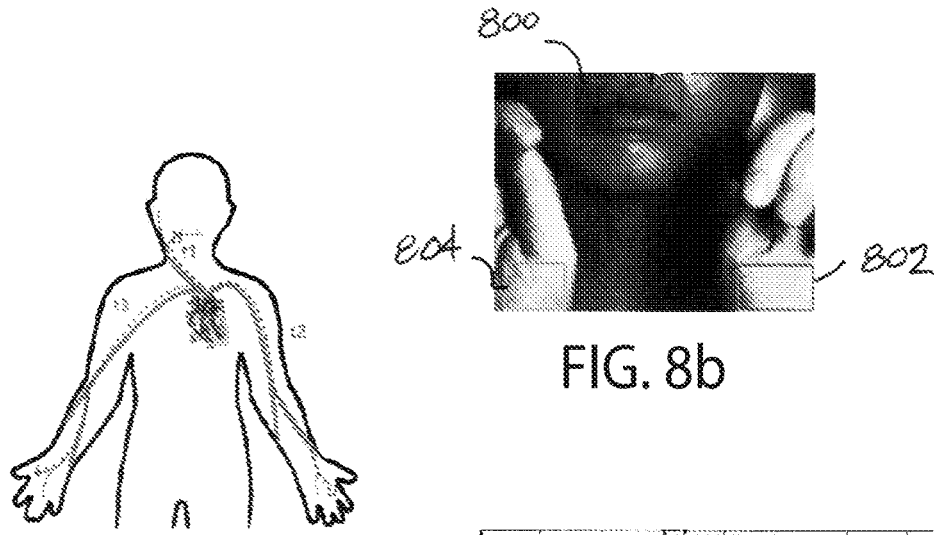
FIG. 8a
FIG. 8b
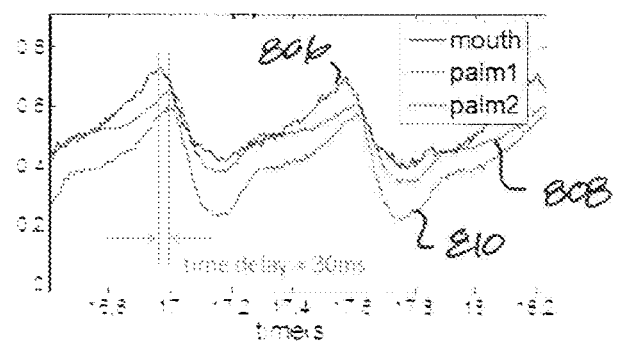
FIG. 8c

SYSTEM AND METHOD FOR NON-CONTACT MONITORING OF PHYSIOLOGICAL PARAMETERS

CROSS-REFERENCE TO RELATED APPLICATIONS

This application is a continuation of U.S. patent application Ser. No. 14/213,236 filed on Mar. 14, 2014 and claims the benefit of U.S. provisional Application No. 61/784,646 filed on Mar. 14, 2013, which is incorporated by reference herein in its entirety.

BACKGROUND

The subject matter disclosed herein relates generally to non-contact and non-invasive monitoring of physiological signals, such as heart rate, pulse transit time and breathing pattern, and/or other physiological parameters of a subject, such as a person.

Monitoring vital physiological signals, such as heart rate, pulse transit time and breathing pattern, are basic requirements in the diagnosis and management of various diseases. Traditionally, these signals are measured only in hospital and clinical settings. An important recent trend is the development of portable devices for tracking the vital physiological signals non-invasively based on optical methods known as photoplethysmography (PPG). These portable devices, when combined with cell phones, tablets or other mobile devices, provide a new opportunity for everyone to monitor one's vital signs any time and any where. These mobile device based efforts can be divided into the following two approaches.

The first approach is optical detection of a person's finger pressed on the portable device or a camera built in the mobile device to perform PPG. While useful, the results are affected by how hard the person presses on the camera, and also by the ambient lighting condition. Further, the need of steady physical contact of person's finger with the portable device makes it impractical for continuously monitoring physiological signals under free-living conditions. The second optical approach is based on a non-contact mode. For example, heart and breathing rates are obtained from images of a person's face, upper arms, and palms recorded with a digital camera, such as a smartphone camera and a webcam. In addition to heart and breathing rates, heart rate variability (HRV) has been analyzed from facial video images. More recently, a near-IR enhanced camera has been used to obtain heart rate from a person's facial area and breathing rate from the person's chest area.

The signals extracted from the images obtained or captured using these imaging-based non-contact approaches contain noise from various sources. To combat the noise issue, at least one conventional method used an independent component analysis (ICA) to separate a multivariate signal into additive subcomponents supposing the mutual statistical independence of the non-Gaussian source signals. Using ICA, heart rate, which typically varies between 0.8-3 Hertz (Hz), has been detected. Further, at least one conventional method determined a movement artifact map by averaging the powers at bandwidths around the heart rate. These efforts helped to minimize unwanted noise in the measured heart rate signals. However, it is much more challenging to track breathing pattern, especially breath-by-breath, because breathing frequency is much lower than the heart rate. In a typical ambient environment, low frequency noise, particularly noise associated with body movement, is much greater than noise at high frequencies.

SUMMARY

In one aspect, a system for monitoring one or more physiological parameters of a subject under free-living conditions includes a camera configured to capture and record a video sequence including at least one image frame of at least one region of interest (ROI) of the subject's body. A computer is in signal communication with the camera to receive signals transmitted by the camera representative of the video sequence. The computer includes a processor configured to process the signals associated with the video sequence recorded by the camera and a display configured to display data associated with the signals.

In another aspect, a method for monitoring a breathing pattern of a subject includes selecting a region of pixels around an edge of each shoulder of the subject to be the regions of interest (ROIs), determining a derivative of the ROIs along a vertical direction to obtained two differential images of the ROIs, determining a position of each shoulder by dividing a differential image of each selected ROI into a top portion and an equal bottom portion along the edge of the shoulder, wherein an intensity of the top portion is dA and an intensity of the bottom portion is dB, and determining a vertical movement of each shoulder for every frame of the video sequence.

BRIEF DESCRIPTION OF THE DRAWINGS

FIG. 7 shows a correlation between exhaled breath volumes obtained from an exemplary differential detection method and an Oxycon device;

FIG. 8(a) shows a PTT definition for three sites of the subject's body;

FIG. 8(b) shows corresponding ROIs of the three sites shown in FIG. 8(a);

FIG. 8(c) shows PPG signals obtained from the ROIs shown in FIG. 8(b), with a time delay of about 30 milliseconds (ms) between PPG signals obtained from the mouth and the palm;

Other aspects and advantages of certain embodiments will become apparent upon consideration of the following detailed description, wherein similar structures have similar reference numerals.

DETAILED DESCRIPTION

Figure 1:
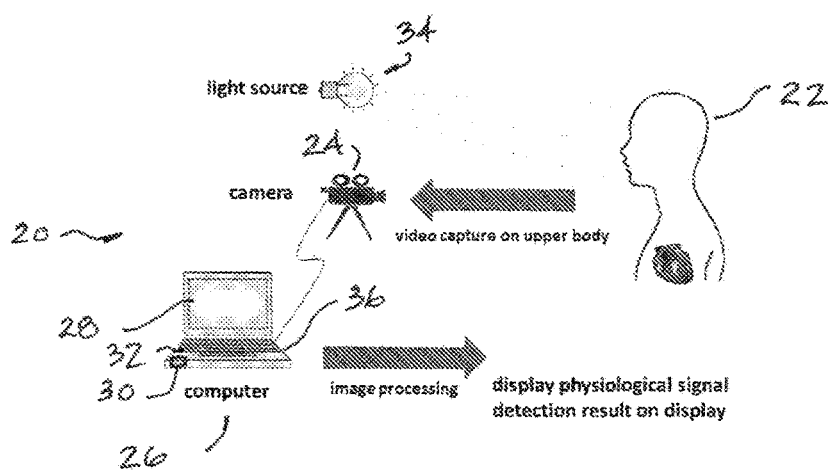
FIG. 1 is a schematic view of an exemplary system configured for non-contact and non-invasive monitoring of physiological parameters of a subject.

The embodiments described herein relate to an optical imaging-based system and associated methods for measuring one or more vital physiological signals of a subject, such as a human patient, including, without limitation, a breathing frequency, an exhalation flow rate, a heart rate, and/or a pulse transit time. In one embodiment, a breathing pattern is tracked based on detection of body movement associated with breathing using a differential signal processing approach. A motion-tracking algorithm is implemented to correct random body movements that are unrelated to breathing. In a particular embodiment, a heart beat pattern is obtained from a color change in selected regions of interest ("ROI") near the subject's mouth, and a pulse transit time is determined by analyzing pulse patterns at different locations of the subject. The embodiments of the imaging-based methods described herein are suitable for tracking vital physiological parameters under a free-living condition. For example, a user can measure his/her vital signs during regular or routine activity, such as working on a computer, or checking a message using a mobile device, such as a cell phone or a tablet. The applications on the computer or mobile device run in the background with no or minimal attention from the user. Additionally, the user does not have to purchase, carry and/or maintain additional devices.

The embodiments described herein provide a method for non-contact monitoring of several physiological signals in real-time by maximizing the signals while minimizing noise due to unwanted body movement. In addition to heart rate and breathing frequency, the exhalation volume flow rate and cardiac pulse transit time (PTT) is obtained in certain embodiments. In one embodiment, movement of one or more selected regions of interest (referred to herein as an "ROI") of the body is detected and used to determine and track a breathing pattern, including a breathing frequency and an amplitude, for example, from which an exhaled volume flow rate is obtained. In a particular embodiment, one or more color changes of one or more selected regions of interest are used to determine heart rate and face paleness. Exhalation flow rate may be an important physiological parameter and is proportional to a subject's metabolic rate. PTT is related to blood pressure pulse wave velocity (PWV), reflecting cardiovascular parameters, such as arterial elasticity and stiffness. Traditionally, PWV has been measured using a galvanometer and ultrasound techniques. Recently, PTT was determined by performing simultaneous ECG and PPG. For example, in certain conventional techniques a contact pulse oximetry is used to determine a difference in PTT of a left index finger and a left second toe. The PTT difference is related to a change in arterial distensibility due to epidurally induced sympathetic block. Conversely, in the embodiments described herein a non-contact optical imaging method is used to determine a PTT difference, along with a breath-by-breath breathing pattern, and an exhalation flow rate.

Referring to FIGS. 1-11, and particularly to FIG. 1, a system 20 is configured to monitor one or more physiological parameters of a subject 22, including, for example, a heart rate (HR), a breathing frequency (BF), an exhalation flow rate and/or a pulse transit time (PTT), by processing images captured with one or more digital cameras using one or more algorithms. In the embodiment shown, the HR and the PTT are detected by tracking an image intensity change of the subject's skin, and the BF and the VE are detected by tracking subtle body movements of the subject associated with breathing.

Referring further to FIG. 1, system 20 includes one or more digital cameras, such as one or more digital cameras 24, in signal communication with a computer 26 having a display 28 configured to display data and parameters associated with signals received from camera 22, such as optical images captured by and acquired from camera 24. Cameras 24 are configured to capture video images and process the video images into associated signals that are then transmitted to computer 26 for further processing before the video images are displayed on display 28. In a certain embodiment, system 20 includes a Logitech colored Webcam (HD 720p), a Pike black and white camera (F-032B), and a Pike color camera (F-032C), used to capture video sequences or images of subject 22, such as video images of the subject's face, palms, and upper body, respectively. Different cameras (colored or black and white) have different inherent noise, but suitable cameras produce satisfactory results in terms of determining the physiological parameters.

In alternative embodiments, a mobile device, such as a cell phone or a tablet, is used by an individual to monitor his or her vital signs at any time and/or any where. These mobile devices are not only equipped with wireless communication capabilities, but also other functions and components, such as a camera, a microphone, an accelerator, and/or a global positioning system (GPS) navigation device, as well as computational power for signal processing.

For example, a face color index can be determined with a mobile device. The color of a human face provides important health information. For example, if someone is sick, his/her face is often pale. Sleep deprivation often shows up as black eyes, and liver, kidney, or thyroid disease may cause chronic black eyes. Further, a person's blood sugar level also has an impact on the color or blackness of the person's eyes. However, accurately capturing the color change under a free-living environment is difficult because of the variability in the lighting condition in most ambient environments. In one embodiment, the method overcomes this difficulty by using light emitted from the mobile device screen (i.e., a cell phone display screen). In one embodiment, an application is downloaded on the mobile device to activate the video recorder to capture and record the video sequence. From the video sequence, a red component from selected regions of interest of the person's face are analyzed. To minimize the effect of ambient light, an image is captured before turning on the screen so that the signals from the uncontrolled ambient light can be removed from the analysis.

Computer 26 includes one or more processors 30 configured to process the signals associated with the video images captured by cameras 24. In one embodiment, each processor 30 receives programmed instructions from software, firmware and data from memory 32 and performs various operations using the data and instructions. Each processor 30 may include an arithmetic logic unit (ALU) that performs arithmetic and logical operations and a control unit that extracts instructions from memory 32 and decodes and executes the instructions, calling on the ALU when necessary. Memory 32 generally includes a random-access memory (RAM) and a read-only memory (ROM). However, there may be other types of memory such as programmable read-only memory (PROM), erasable programmable read-only memory (EPROM) and electrically erasable programmable read-only memory (EEPROM). In addition, memory 32 may include an operating system, which executes on processor 30. The operating system performs basic tasks that include recognizing input, sending output to output devices, such as display 28, keeping track of files and directories and controlling various peripheral devices.

As used herein, references to "processor" are to be understood to refer to central processing units, microprocessors, microcontrollers, reduced instruction set circuits (RISC), application specific integrated circuits (ASIC), logic circuits and any other circuit or processor capable of executing the functions described herein. Memory 32 may include storage locations for the preset macro instructions that may be accessible using a preset switch, for example.

As used herein, references to "software" and "firmware" are interchangeable, and are to be understood to refer to and include any computer program stored in memory for execution by processor 30, including RAM memory, ROM memory, EPROM memory, EEPROM memory, and non-volatile RAM (NVRAM) memory. The above memory types are exemplary only, and are thus not limiting as to the types of memory usable for storage of a computer program. In various embodiments, processor 30 and memory 32 are located external to camera 24 such as in computer 26 or another suitable standalone or mainframe computer system capable of performing the functions described herein. In one embodiment, video images are transferred to memory 32 or digitized. In an alternative embodiment, processor 30 is located within camera 24. In this embodiment, processor 30 may be in signal communication with a display of the camera 24 or mobile device in which the camera is housed or in signal communication with an external computer having a display configured to display data associated with the signals generated by camera 24 and processed by processor 30.

In one embodiment, the video sequences or images are taken under ambient light condition. In a particular embodiment, one or more controlled light sources 34, such as one or more light emitting diode (LED) source and/or a suitable desk lamp, are used. Subject 22 sits at a distance of 30 centimeters (cm) to 80 centimeters, and, more particularly, 50 cm from a lens of camera 24 to ensure a good quality and clear focus for the captured images and associated signals. In one embodiment, the imaging method uses only ambient light of low-cost CMOS imagers (e.g., webcam), which is suitable for tracking physiological parameters under free-living conditions. The method can be readily adapted to the mobile platform, such as cell phones, tablets, etc. with a built-in camera as described above. The use of personal mobile devices reduces the privacy concern of imaging-based detection. Because the approach is noninvasive, an additional benefit is that the results truly reflect the person's health status, without the known "white coat effect," a phenomenon in which patients exhibit elevated blood pressure in a clinical setting.

A user interface 36, such as a Matlab-based user interface or other suitable user interface, analyzes the captured video sequences and data. In one embodiment, user interface 36 is capable of showing a live or real time video sequence of subject 22, which allows a selection of regions of interest (ROI), and for processor 30 to perform signal processing of the data in the ROIs to determine the heart beat and breathing signals independently, and display the results in real time on display 28.

Figures 2A, 2D:
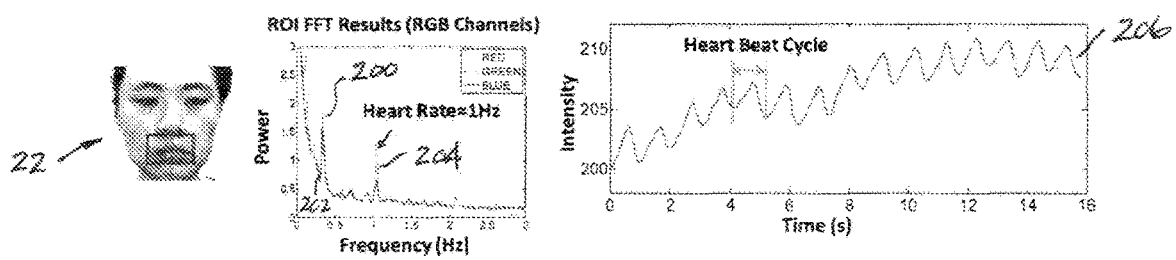
FIG. 2(a) shows an original image with a region of interest (ROI) (blue rectangle) near a mouth of the subject (shown on the left portion of FIG. 2(a)) and a Fast Fourier Transform (FFT) spectrum of the ROI (shown on the right portion of FIG. 2(a)) illustrating red, green and blue lines representing the R, G and B color channels, respectively.
FIG. 2(d) shows a heart beat waveform obtained with an exemplary method.
Figures 2B, 2C, 2E:
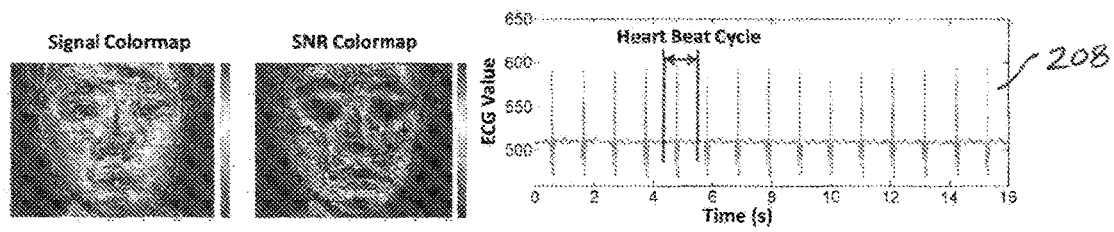
FIG. 2(b) shows a colormap of an FFT peak amplitude in each pixel at a heart beating frequency (heart rate) illustrating a color scale from blue to red indicating the FFT peak amplitude at heart rate.
FIG. 2(c) shows a signal-to-noise ratio (SNR) colormap at heart rate.
FIG. 2(e) is a heart beat detection validation illustrating a heart beat waveform obtained from a commercial device.

Heart Beat Monitoring. In one embodiment, camera 22 captures and records a video sequence or video images of a subject's face for a suitable time period, such as 30 seconds. Processor 30 is configured to perform a Fast Fourier Transform (FFT) on the intensity signal averaged over all the pixels in each selected ROI to determine the frequency components of the video signal within a noisy time domain signal. In certain embodiments, a longer recording time may produce a better signal, but is less user friendly as it requires a longer testing time. The FFT spectrum of the ROI clearly reveals the heart beat signal as a peak at a frequency corresponding to the heart rate. In order to optimize the signal-to-noise ratio (SNR), the results of a red channel 200, a blue channel 202, and a green channel 204 are compared, and green channel 204 has been found to give the strongest heart beat signal, or the largest peak amplitude in the FFT spectrum, as shown in FIG. 2(a). One possible reason is that oxygenated hemoglobin absorbs green light more than red light and penetrates deeper into the subject's skin when compared to blue light. Because the SNR may also depend on the selection of ROI, in one embodiment the peak amplitude in each pixel is extracted and plotted on a color-map to analyze the variation of the heart beat signal in different areas of the face as shown in the signal colormap of FIG. 2(b). The areas around the subject's lips and nose regions have larger heart beat amplitudes, which is consistent with the fact that these regions have more blood vessels. Referring to FIG. 2(b), the eye regions and the face edges also appear to have large heart beat amplitudes, which is due to body movement, rather than real heart beat signals. This conclusion is supported by the SNR colormap shown in FIG. 2(c), obtained by normalizing the peak amplitude in the FFT spectrum of each pixel with the noise level near the peak. As shown in FIG. 2(c), the SNR colormap shows that the regions around the eyes and the edges of the subject's face have rather low SNR values.

The signal analysis described herein leads to a conclusion that the region around the lips gives the strongest and most stable heart beat signal. For real time determination of heart rate, the region around the lips is selected with an ROI size of 40×80 pixels, and green channel 204 of the ROI is analyzed for heart beat detection. In one embodiment, the green channel signal is first averaged within the ROI, and then processed by a low-pass filter with a cut-off frequency of 2 Hz to remove background noise at a high frequency. FIG. 2(d) shows a heart beat signal 206 obtained by such process. As described herein and referring to FIG. 2(e), a Zephyr wearable device or other suitable device can be used to obtain heart beat waveforms 208 as a reference to validate the results herein. The heart rate calculated from the ECG measured by the Zephyr wearable device, as shown in FIG. 2(e), is comparable to the heart rate obtained with methods as described herein.

Breathing Pattern Monitoring. Unlike heart rate monitoring, the breathing pattern can be determined according to one embodiment by detecting and analyzing the body movement associated with breathing. Different parts of the body move with breathing differently. For example, the chest and the abdomen will expand and contract, the shoulder and the head will move, such as in a vertical direction up and down Additionally, a person's facial features will change or move with the associated movement of the shoulder and the head. Conventional methods for measuring the body movement associated with breathing use a device worn by the user. This approach, as discussed above, is inconvenient.

Figure 3A:
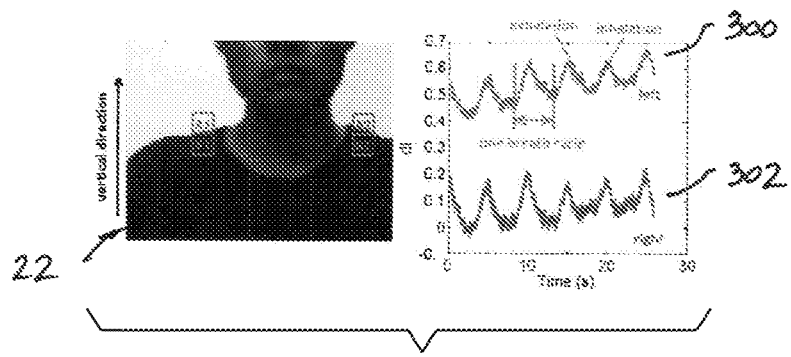
FIG. 3(a) illustrates tracking shoulder movement of the subject to detect a breathing pattern, wherein the left panel of FIG. 3(a) shows a selected ROI on each shoulder (red box), and each ROI is divided into two sub-regions, sub-region A and sub-region B, along a vertical direction and the right panel of FIG. 3(a) shows corresponding breathing cycles from the ROIs using a detection method.

The subject's chest and abdomen may have the largest movement with breath, but these regions are not easily accessible to camera 22 for imaging under natural and free-living conditions. For this reason, movement of the subject's face, neck and upper body is detected and analyzed to determine the breathing pattern. In this embodiment, the body movement is measured via a sequence of images or a video including a plurality of images, which does not involve direct, physical contact with the subject, and is thus less invasive, and tracks the breathing pattern with a suitable device, such as a built-in camera of a computer or a built-in camera of a mobile device. In one embodiment, a region of 40×40 pixels around an edge of each shoulder of subject 22 is selected to be the ROIs for breathing detection, as shown in FIG. 3(a)(left panel). A derivative of the ROIs is taken along a vertical direction to obtained two differential images of the ROIs. The edges of the shoulders in the differential images are revealed as bright lines in FIG. 3(b).

Figure 3B:
FIG. 3(b) shows a zoomed-in image showing the subject's left shoulder in the left panel of FIG. 3(b) and the right panel of FIG. 3(b) shows a derivative image with respect to the vertical direction, wherein the shoulder edge is shown as a bright line.
Figure 4:
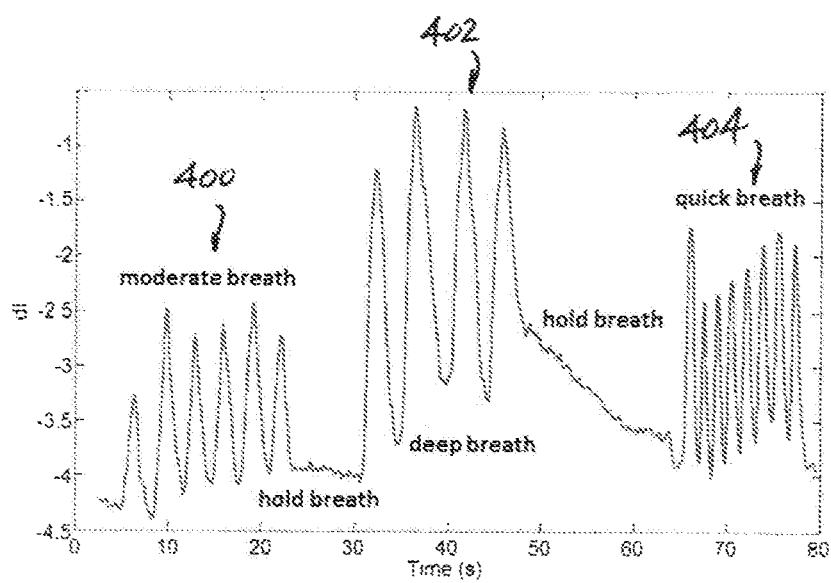
FIG. 4 shows different breathing patterns obtained by an exemplary differential method.

The locations of the bright lines shown in FIG. 3(b) indicate the respective positions of the edges of the subject's left shoulder and right shoulder. To accurately determine the shoulder positions, the differential image of each selected ROI is divided into two equal portions along the shoulder edge. An intensity of a top portion is referred to as dA, and an intensity of a bottom portion is referred to as dB. When the shoulders move up and down with breathing, dA increases (or decreases) and dB decreases (or increases). The vertical movement of shoulders can be determined by:

$$dI = \frac{dA - dB}{dA + dB}.$$ Eq. (1)

A difference, dA−dB, in Eq. 1 is sensitive to the vertical movement, and also immune of common noise in dA and dB. Dividing dA−dB by dA+dB further reduces noise associated with intensity fluctuations of light source 34. dI is calculated for every frame of the video sequence, and plotted against time after applying a low-pass filter with a cut-off frequency of 2 Hz, as shown in FIG. 3(a)(right panel).

Shown in FIG. 3(a)(right panel) is an example of breathing waveforms obtained with the method described above, wherein the downhill cycles correspond to exhalation periods when the thoracic cavity is shrinking and the shoulders move downwards, and the uphill cycles correspond to inhalation periods when the thoracic cavity is expanding and the shoulders move upwards. The breathing pattern obtained from both the left shoulder 300 and the right shoulder 302 are shown in FIG. 3(a)(right panel), which are in good agreement with each other.

To further demonstrate the reliability of the method for real-time monitoring of a breathing pattern, the subject is instructed to change his/her breathing pattern intentionally. Initially, the subject breathed normally for 6 cycles, as indicated by reference number 400, followed by 4 cycles of deep breathing, as indicated by reference number 402, and then 8 cycles of rapid breathing, as indicated by reference number 404. The results shown in FIG. 4 demonstrate that the described method successfully captures the breathing pattern variations.

Figure 5:
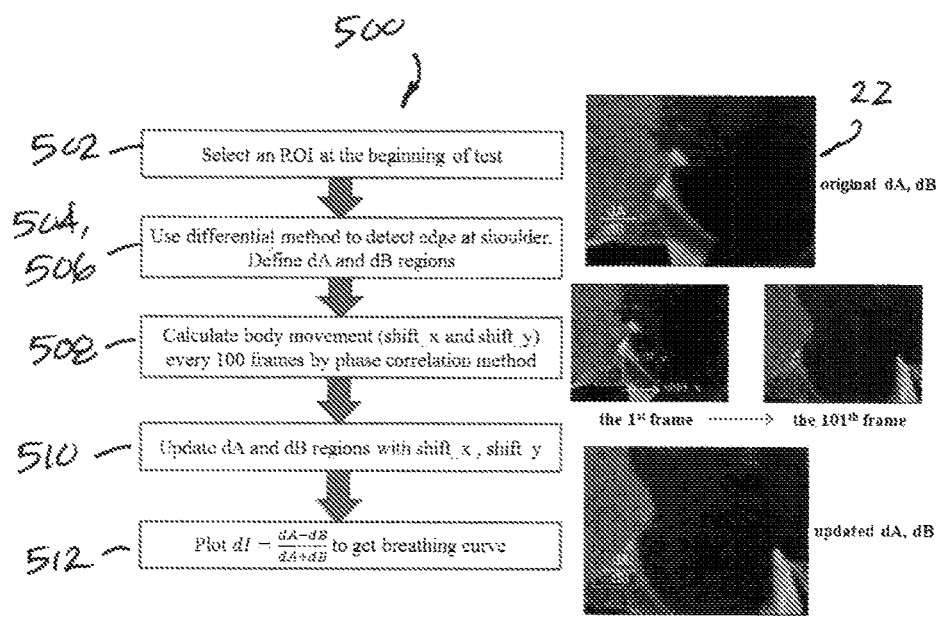
FIG. 5 shows a workflow for a method of tracking body movement using a motion tracking algorithm.

The accuracy of a breathing pattern measurement may be affected by large body movements unrelated to breathing during these measurements. In one embodiment, a method 500 implements a motion-tracking algorithm to correct such motion artifacts based on a phase correlation method. The motion-tracking algorithm checks a shift of the ROIs due to the body movement at a suitable time interval, for example, every two seconds, and corrects the shift of each ROI by updating a new location of the ROI. Referring to FIG. 5, an ROI is selected 502 to begin method 500. A differential method is used to detect an edge at a shoulder of the subject 504 and region dA and region dB are defined 506. Body movement is calculated every 100 frames of the video sequence, for example, by a phase correlation method 508. In this embodiment, the body movement is calculated based on a shift in an x direction, indicated as shift_x, and a shift in a y direction, indicated as shift_y. Region dA and region dB are updated 510 with shift_x and shift_y. dI as calculated using Eq. 1 above is plotted 512 to generate a breathing curve.

Figure 6A:
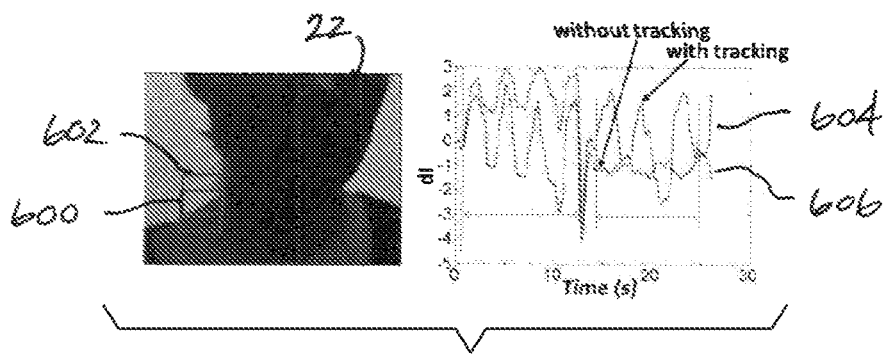
FIG. 6(a) illustrates the effectiveness of an exemplary motion tracking algorithm for detecting a breathing pattern detection, wherein the left panel shows an image of a subject with a selected ROI on the subject's left shoulder and the right panel shows breathing patterns with the motion-tracking algorithm (blue curve) and without the motion-tracking algorithm (red curve)

The effectiveness of this method implementing the motion-tracking algorithm is shown in FIG. 6(a), which compares the results with and without the motion-tracking algorithm. The left panel of FIG. 6(a) shows an image of subject 22 with a selected ROI on the subject's left shoulder. When the exemplary motion-tracking algorithm as described herein is enabled, the ROI follows the body movement (blue box 600). In contrast, when the motion-tracking algorithm is disabled, the ROI is fixed in the image and the shoulder may move out of the ROI (red box 602). The right panel of FIG. 6(a) shows breathing patterns with the motion-tracking algorithm (blue curve 604) and without the motion-tracking algorithm (red curve 606). Without applying the motion-tracking algorithm, the measured breathing signal was overwhelmed by the body movement. In contrast, the breathing pattern is clearly observed with the implementation of the motion-tracking algorithm. The algorithm worked effectively at least in part because the breathing-related body movement of the shoulders has a small amplitude and is primarily in the vertical direction, which is different from the relatively large body movement that may occur in all directions and at time scales different from the regular breathing.

Figure 6B:
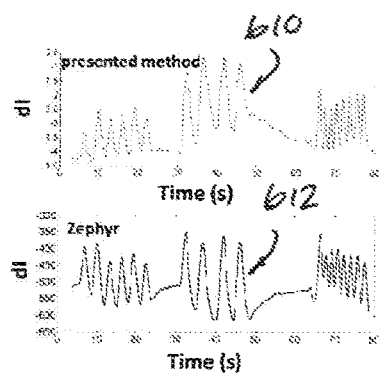
FIG. 6(b) illustrates a comparison of breathing patterns obtained with an exemplary method as described herein (red line) and with a Zephyr device (black line)
Figure 6C:
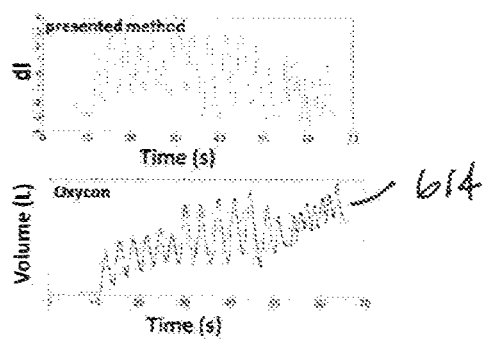
FIG. 6(c) illustrates a comparison of breathing patterns obtained with an exemplary method as described herein (red line) and an Oxycon device (black line)

Referring to FIGS. 6(b) and 6(c), the breathing pattern detection method as described herein is validated by comparing the results of a breathing pattern obtained with the exemplary method (red line 610) and a breathing pattern obtained with a Zephyr device (black line 612), as shown in FIG. 6(b), and a breathing pattern obtained with an Oxycon device (black line 614), as shown in FIG. 6(c). The results obtained with the image processing method described herein are in excellent agreement with the two different reference technologies, not only in a breathing frequency but also in a relative breathing amplitude.

Determination of Exhalation Flow Rate. The amplitude of the breathing-related shoulder movement is associated with an exhalation volume per breathing cycle, or an exhalation flow rate. The relationship was examined by plotting the amplitude vs. exhalation flow rate obtained with the Oxycon instrument. Six tests were carried out, and in each test, the subject changed the exhalation flow rate. FIG. 7 shows a plot of a breathing amplitude (from the differential signal, dI, (peak to peak)) of the tests vs. an exhaled breath volume obtained with the Oxycon instrument (Oxycon volume (L)), which shows a linear relationship ($R^2=0.81$) between dI and the exhaled breath volume. This observation demonstrates a method to remotely determine exhalation flow rate under a free-living condition. FIG. 7 shows the correlation between the exhaled breath volume obtained from the differential detection method and the commercially available Oxycon instrument. In the differential detection method, the exhaled breath volume is taken from the shoulder movement, or dI. Data from 6 tests can be fit with a linear curve. For every unit of dI, the volume change is about 0.15 Liters (L).

In one embodiment, an energy expenditure based on the breathing frequency and amplitude is determined. One suitable equation for determining the energy expenditure is indirect calorimetry, which measures consumed oxygen and produced carbon dioxide rate using the Weir equation. The equation takes the form of:

$$EE(kCal/day)=[3.9(VO_2)+1.1(VCO_2)]\times 1.44, \quad \text{Eq. (2)}$$

where $VO_2$ is oxygen consumption rate (ml/min.), and $VCO_2$ is carbon dioxide production rate (ml/min.), respectively. $VO_2$ and $VCO_2$ can be further expressed in terms of $V_E$, and given by:

$$VO_2=V_E\times(0.2093-FO_2) \text{ and} \quad \text{Eq. (3)}$$

$$VCO_2=V_E\times(FCO_2-0.0003), \quad \text{Eq. (4)}$$

where $FO_2$ and $FCO_2$ are a fraction of oxygen and a fraction of carbon dioxide, respectively, in an exhaled breath. For most people, $FO_2$ and $FCO_2$ tend to be constant, at least under the same conditions. This means that the energy expenditure is simply proportional to $V_E$, which is given by:

$$V_E=V_b*f_b, \quad \text{Eq. (5)}$$

where $V_b$ is a volume of exhaled air per breathing cycle, and $f_b$ denotes a breathing frequency. Alternatively, $V_E$ can be expressed as a total exhaled volume for a period over time.

In one embodiment, $V_b$ is linearly correlated to a breathing amplitude determined with the methods disclosed above as shown in FIG. 12. From this relationship, $V_b$ and, thus, $V_E$, is determined and the energy expenditure is determined from Equation 2.

Pulse Transit Time. In one embodiment, a non-contact optical imaging method is also used to determine pulse transit time (PTT) related information. The variations in PTT of different body sites are obtained by analyzing a time difference of PPG signals. In FIG. 8(a), the PTT from the subject's heart to the subject's mouth, and from the subject's heart to the subject's left palm and right palm were indicated by t1, t2, and t3, respectively. The corresponding ROI selections of three locations from the video sample are shown in FIG. 8(b) as three rectangles having different colors, namely ROI selection 800, ROI selection 802, and ROI selection 804. The PPG signals obtained from the ROIs were plotted in FIG. 8(c). Time differences were found between PPG signals from different regions of the subject's body in every heart cycle. The PPG signal detected from the mouth area (blue curve 806) arrived earlier than the PPG signals detected from the left palm area (red curve 808) and the right palm area (green curve 810). A sample of the delay is shown in FIG. 8(c) to illustrate a PTT difference between the mouth and the palms from signals obtained from the ROIs. The time delay is about 30 milliseconds (ms) between the PPG signals obtained form the mouth and the palms. The PTT difference was not obvious between left and right palms.

Figure 9A:
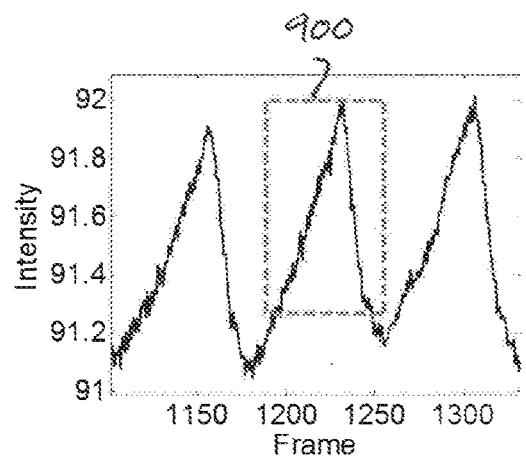
FIG. 9(a) shows an estimate peak location for a single cycle of a PPG signal by using a linear curve fitting method, wherein one cycle from the PPG signal is taken and 2 linear curves (black dash lines) are used to fit the original signal from a left part (red) and a right part (blue), independently.
Figure 9B:
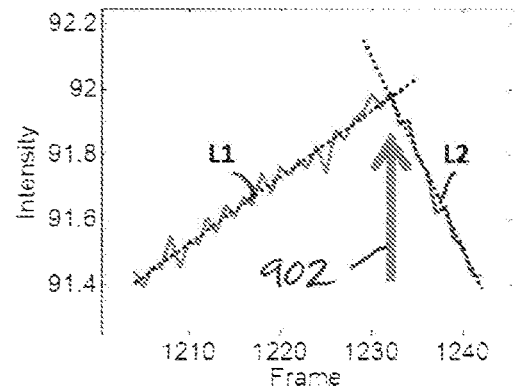
FIG. 9(b) shows a point of intersection of 2 linear curves (green arrow) at the estimated peak location in that particular heart beat cycle.

Several signal processing algorithms can be utilized to determine the time differences in PTT among the different body sites. In one embodiment, a first algorithm is based on comparing peak locations of different PPG signals using a linear curve fitting method. FIGS. 9(a) and 9(b) show an estimated peak location for a single cycle of a PPG signal using a linear curve fitting method. FIG. 9(a) shows an original PPG signal sample including one heart beat cycle from a PPG signal obtained from one subject. The heart beat cycle is selected by a dash red rectangle 900 for further analysis. The peak location of the selected signal is estimated by fitting two linear curves L1 and L2 (black dashed lines). L1 is positioned on a rising edge (left portion of the peak) and L2 is positioned on a falling edge (right portion of the peak) of the signal as shown in FIG. 9(b). The point of intersection (indicated by the green arrow 902) of the two linear curves L1 and L2 is the estimated peak location in the selected heart beat cycle. PTT differences were determined by comparing the peak locations of PPG signals obtained at different body locations (e.g., the subject's mouth and the subject's fingers).

To validate the results, simultaneous measurements of the physiological signals were carried out with different reference technologies. For heart rate measurement, a Zephyr ECG was used. For breathing pattern measurement, two reference technologies, viz., a Zephyr wearable device and an Oxycon metabolic analysis instrument, were used. The Zephyr device used a movement sensor integrated in a belt wrapped around the subject's chest. Because the Zephyr device does not provide exhaled flow rate, the Oxycon instrument is used to measure both the breathing frequency and the exhalation volume flow rate via a turbine flow meter attached to a mask worn by the subject. To validate PTT results, several feature extraction algorithms can be used, and EPIC Motion Sensors (PS25451).

As shown in Table I below, nine tests taken from one subject were analyzed to obtain the average value of PTT difference between the subject's mouth area and the subject's palm areas. Each test lasted for 30 seconds. The PTT difference for each test is an average result from all the available heart beat cycles in that time period. Table I shows PPG delay estimation results among different sites. The values are calculated based on a linear curve fitting method. The estimated delay values obtained form a facial area to two palm areas are similar, about 30-31 milliseconds (ms).

TABLE I

| Test No. | Heart Rate (bpm) | PTT Difference from Left Palm to Mouth (ms) | PTT Difference from Right Palm to Mouth (ms) |
|---|---|---|---|
| 1 | 72 | 22.50 | 22.28 |
| 2 | 78 | 34.50 | 32.37 |
| 3 | 78 | 28.36 | 29.35 |
| 4 | 72 | 30.39 | 32.23 |
| 5 | 72 | 23.35 | 27.82 |
| 6 | 71 | 33.97 | 35.64 |
| 7 | 106 | 25.99 | 28.26 |
| 8 | 96 | 34.56 | 36.04 |
| 9 | 96 | 34.13 | 35.61 |
| Average | | 29.75 | 31.07 |
| SD/Average | | 16% | 15% |

Matlab functions, findpeaks and xcorr, were also used to estimate the value of PTT difference. Function findpeaks provides the peak location of the input data by searching for the local maximum value of the sequence. Function xcorr realizes phase shift estimation between two signals by taking their convolution and searching for the delay that gives the largest convoluted result. However, the standard deviations of the calculated PTT differences obtained from these two methods were higher than the standard deviation obtained from the first one (linear curve fitting method). Therefore, the first method was used to estimate the PTT differences among different body sites. Test results in Table I show that the difference in PTT between the palm and the mouth is about 30 ms. The results are consistent with the values of PTT difference between ears and fingers reported by other researchers.

Small-Scale Pilot Study. To demonstrate the robustness of the developed methods to monitor physiological signals, a small-scale pilot study was conducted for statistical analyses. Ten participants were enrolled in the Institutional Review Board (IRB) study, which was approved by Arizona State University. The participants were of different genders (6 males, 4 females), age (27.3±4.5 years old, mean±S.D.), ethnic profiles, and skin colors. Informed consents were obtained from all participants following approved protocol.

Figure 10:
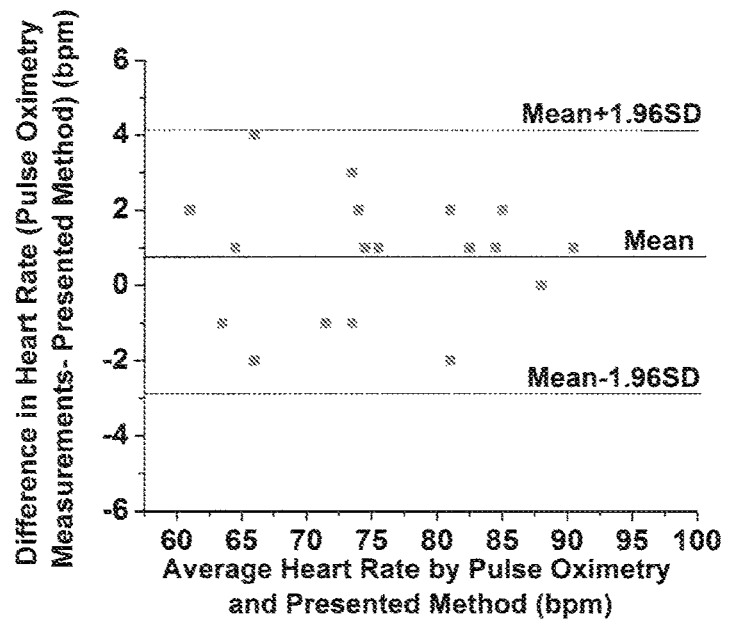
FIG. 10 illustrates Bland-Altman plots showing an average of a heart rate measured by a commercial pulse oximetry and an exemplary method as described herein, plotted against a difference between them.
Figure 11:
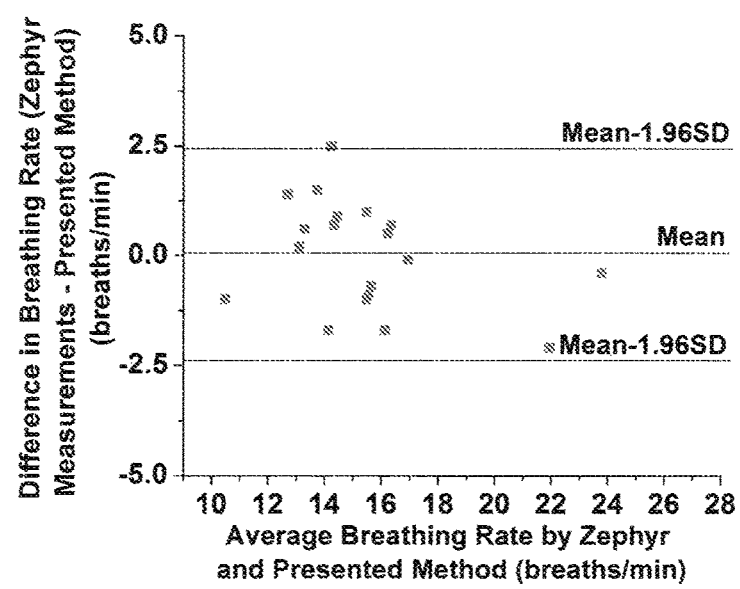
FIG. 11 illustrates Bland-Altman plots showing an average of a breathing rate measured by a commercial Zephyr device and an exemplary method as described herein, plotted against a difference between them.

Bland-Altman plots were used to analyze the agreements between presented physiological signal detection methods and reference technologies. FIG. 10 shows the Bland-Altman plot for heart rate detection. The differences between the breathing rate measured by the non-contact method described herein and the breathing rate measured by a commercial pulse oximetry (y-axis) were plotted against the average breathing rate measured by the two methods (x-axis). The mean difference was 0.86 beats per minute (bpm) with 95% limits of agreement (±1.96 standard deviation) at −2.47 bpm and 4.19 bpm. The root-mean-square error (RMSE) was 1.87 bpm and r was 0.98 ($p<0.001$). FIG. 11 shows the Bland-Altman plot for breathing rate detection. The differences between the breathing rate measured by the non-contact method described herein and the breathing rate measured by a Zephyr device (y-axis) were plotted against the average breathing rate measured by the two methods (x-axis). The mean difference was 0.02 breaths/minute (min.) with 95% limits of agreement (±1.96 standard deviation) at −2.40 breaths/min. and 2.45 breaths/min. RMSE was 1.20 breaths/min. and r was 0.93 ($p<0.001$).

Both the method described herein and the reference technologies can introduce error to the test results. For statistical analyses, $p<0.05$ is considered to be a significant correlation between two compared methods. So the overall error rates were acceptable. A pilot study was also conducted for PTT difference calculation. Ten tests were taken from 4 subjects. The average PTT difference between the mouth area and the palm areas was about 30-40 ms, as shown in Table II. Table II shows PTT difference estimate results among four subjects. The values were calculated based on a linear curve fitting method. The average PTT difference between the mouth area and the palm areas was about 35 ms from the left palm area to the mouth area and 37 ms from the right palm area to the mouth area.

TABLE II

| Test No. | Gender | PTT Difference from Left Palm to Mouth (ms) | PTT Difference from Right Palm to Mouth (ms) |
|---|---|---|---|
| 1 | Female | 29.75 | 31.07 |
| 2 | Female | 35.02 | 32.06 |
| 3 | Male | 32.96 | 41.67 |
| 4 | Male | 42.03 | 43.29 |
| Average | | 34.94 | 37.02 |
| SD/Average | | 15% | 17% |

The embodiments described herein demonstrate exemplary optical imaging-based methods for non-contact monitoring of physiological signals, including, for example, breathing frequency, exhalation flow rate, heart rate, and pulse transit time, by detecting facial color changes associated with blood circulation and body movement associated with breathing. By implementing differential detection and motion-tracking algorithms, the breathing frequency and the exhalation volume flow rate are accurately tracked, which is robust against moderate body movements unrelated to breathing. The physiological signals measured by the imaging methods are in excellent agreement with those obtained using reference technologies. As demonstrated herein, the difference in pulse transit time can be determined by the non-contact imaging method and the results are comparable to the related values reported by other literature. Furthermore, results of a small-scale pilot study involving participants of different ethnic profiles, sex and ages demonstrate the basic principle of the optical imaging methods.

The described system and methods are not limited to the specific embodiments described herein. In addition, components of each system and/or steps of each method may be practiced independent and separate from other components and method steps, respectively, described herein. Each component and method also can be used in combination with other systems and methods.

The foregoing description of embodiments and examples has been presented for purposes of illustration and description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent devices by those of ordinary skill in the art. Rather, it is hereby intended the scope be defined by the claims appended hereto. Additionally, the features of various implementing embodiments may be combined to form further embodiments.

What is claimed is:

1. A system for monitoring a subject under free-living conditions, the system comprising:

at least one camera configured to acquire from the subject a video sequence having one or more image frames; and a computer, in signal communication with the at least one camera, and configured to receive therefrom signals associated with the video sequence, the computer including:

a processor configured to apply a differential signal processing to signals associated with at least one portion of the subject's body to determine a breathing pattern of the subject based on a movement of the at least one portion of the subject's body, wherein the processor is configured to assemble a breathing waveform describing the breathing pattern by:

a) generating, using an image frame in the video sequence, a second image indicating an edge of the subject's body, wherein the second image is generated by taking a derivative of a region of interest along a line within the region of interest to identify an edge of the subject's body;

b) selecting, using the second image, at least one region of pixels around an edge of the subject's body;

c) dividing each selected region of pixels of the second image into at least two defined portions, wherein a first portion and a second portion of the at least two defined portions are divided by an edge of the subject's body;

d) quantifying a body movement of the subject's body based on a shift in an x direction of the region of interest featuring the subject's body relative to the image frame and a shift in a y direction of the region of interest featuring the subject's body relative to the image frame; and e) updating the first portion and the second portion based on the quantified body movement; and a display configured to at least display data indicative of the breathing pattern wherein the processor is further configured to assemble a breathing waveform describing the breathing pattern by:

a) computing, for each selected region of pixels, a differential defined by $$dI = \frac{dA - dB}{dA + dB}$$

indicative of a difference in intensity between the first portion represented by dA and the second portion represented by dB, wherein a denominator dA+dB reduces noise associated with an intensity fluctuation of a light source;

b) calculating a plurality of differentials dI for a plurality of image frames in the video sequence; and c) assembling a breathing waveform using the computed plurality of differentials dI.

2. The system of claim 1, wherein the signals associated with the at least one portion of the subject's body comprise signals from a head, a face, a neck, a shoulder, a chest, a torso, an arm, a palm, or a combination thereof.

3. The system of claim 1, wherein the computer is external to the at least one camera.

4. The system of claim 1 wherein the processor is further configured to process received signals to determine one or more physiological parameters selected from a list consisting of a heart rate, a breathing amplitude, a breathing frequency, an exhalation flow rate and a pulse transit time.

5. The system of claim 4 wherein the processor is further configured to detect the heart rate and the pulse transit time by tracking an image intensity change of the subject's skin.

6. The system of claim 4 wherein the processor is further configured to determine the breathing frequency, the breathing amplitude and the exhalation flow rate from the breathing pattern.

7. The system of claim 1 wherein the processor is configured to determine the breathing pattern by determining a vertical movement of the at least one portion of the subject's body.

8. The system of claim 1, wherein the processor is further configured to filter the breathing waveform by applying a low-pass filter.

9. The system of claim 8, wherein the low-pass filter has a cut-off frequency of approximately 2 Hz.

10. The system of claim 1, wherein the at least one camera is housed within a mobile device.

11. The system of claim 1 further comprising a light source configured to illuminate the at least one portion of the subject's body.

12. The system of claim 1, wherein the processor is further configured to compute a Fast Fourier Transform (FFT) spectrum, using an intensity signal associated with one or more pixels associated with the subject's face, to determine a heart rate of the subject.

13. The system of claim 12, wherein the processor is further configured to generate, using the FFT spectrum, a color map indicating a variation of a peak amplitude of the FFT spectrum at the heart rate across different areas of the subject's face.

14. The system of claim 1, wherein the processor is configured to determine, using the breathing pattern, a volume flow rate of exhaled air to determine an energy expenditure.

15. The system of claim 1, wherein the processor is further configured to determine variations in pulse transit times in the subject by analyzing a time difference between photoplethysmography (PPG) signals associated with different body sites.

16. The system of claim 1 further comprising a user interface configured for selecting at least one region of interest (ROI) in the subject's body using the video sequence.

17. The method of claim 1, wherein the edge is identified within the region of interest by identifying a corresponding change in the derivative of the line within the region of interest.

18. The method of claim 1, wherein the body movement is devoid of a respiration of the subject.

19. A method for monitoring a subject under free-living conditions, the method comprising:

acquiring, using a camera, a video sequence indicating at least one portion of the subject's body;

selecting at least one region of interest (ROI) in the subject's body using the video sequence;

applying, using the computer, a differential edge detection process to identify a variation in image intensities corresponding to the selected ROI to determine a body movement of the subject;

a) generating, using an image frame in the video sequence, a second image indicating an edge of the subject's body, wherein the second image is generated by taking a derivative of a region of interest along a line within the region of interest to identify an edge of the subject's body;

b) selecting, using the second image, at least one region of pixels around an edge of the subject's body;

c) dividing each selected region of pixels of the second image into at least two defined portions, wherein a first portion and a second portion of the at least two defined portions are divided by an edge of the subject's body;

d) quantifying a body movement of the subject's body based on a shift in an x direction of the region of interest featuring the subject's body relative to the image frame and a shift in a y direction of the region of interest featuring the subject's body relative to the image frame relative to the image frame; and e) updating the first portion and the second portion based on the quantified body movement;

determining a breathing pattern based on the body movement; and generating a report indicative of the breathing pattern of the subject, wherein the method further comprises assembling a breathing waveform describing the breathing pattern by:

a) computing, for each selected region of pixels, a differential defined by $$dI = \frac{dA - dB}{dA + dB}$$

indicative of a difference in intensity between the first portion represented by dA and the second portion represented by dB, wherein a denominator dA+dB reduces noise associated with an intensity fluctuation of a light source;

b) calculating a plurality of differentials dI for a plurality of image frames in the video sequence; and c) assembling a breathing waveform using the computed plurality of differentials dI.

20. The method of claim 19, wherein at least one portion of the subject's body comprises a head, a face, a neck, a shoulder, a chest, a torso, an arm, a palm, or a combination thereof.

21. The method of claim 19, wherein the method further comprises processing the video sequence to determine one or more physiological parameters selected from a list consisting of a heart rate, a breathing amplitude, a breathing frequency, an exhalation flow rate, an exhalation volume, an energy expenditure, and a pulse transit time.

22. The method of claim 19, wherein the method further comprises updating the first portion and the second portion based on the quantified body movement approximately every 100 frames of the video sequence.

23. The method of claim 19, wherein the method further comprises a time delay between photoplethysmography (PPG) signals associated with different body sites, the PPG signals being obtained using the video sequence.

24. The method of claim 19, wherein the body movement is devoid of a respiration of the subject.

25. A system for monitoring a subject under free-living conditions, the system comprising:

at least one camera configured to acquire from the subject a video sequence having one or more image frames; and a computer, in signal communication with the at least one camera, and configured to receive therefrom signals associated with the video sequence, the computer including:

a processor configured to apply a differential signal processing to signals associated with at least one portion of the subject's body to determine a breathing pattern of the subject based on a movement of the at least one portion of the subject's body, wherein the processor is configured to assemble a breathing waveform describing the breathing pattern by:

a) generating, using an image frame in the video sequence, a second image indicating an edge of the subject's body, wherein the second image is generated by taking a derivative of a region of interest along a line within the region of interest to identify an edge of the subject's body;

b) selecting, using the second image, at least one region of pixels around an edge of the subject's body;

c) dividing each selected region of pixels of the second image into at least two defined portions, wherein a first portion and a second portion of the at least two defined portions are divided by an edge of the subject's body;

d) quantifying a body movement of the subject's body based on a shift in an x direction of the region of interest featuring the subject's body relative to the image frame and a shift in a y direction of the region of interest featuring the subject's body relative to the image frame; and e) updating the first portion and the second portion based on the quantified body movement; and a display configured to at least display data indicative of the breathing pattern, wherein the processor is further configured to assemble a breathing waveform describing the breathing pattern by:

a) computing, for each selected region of pixels, a differential defined by $$dI = \frac{dA - dB}{dA + dB}$$

indicative of a difference in intensity between the first portion represented by dA and the second portion represented by dB, wherein a denominator dA+dB reduces noise associated with an intensity fluctuation of a light source;

b) calculating a plurality of differentials dI for a plurality of image frames in the video sequence; and c) assembling a breathing waveform using the computed plurality of differentials dI, and wherein dA is a value describing an intensity of a first portion of the at least two defined portions and wherein dB is a value describing an intensity of a second portion of the at least two defined portions.

* * * * *